United States Patent
Anderson (10) Patent No.: US 9,901,167 B2
(45) Date of Patent: Feb. 27, 2018

(54) FILTER ASSEMBLY FOR USE WITH A WIDE-MOUTH FERMENTATION CARBOY

(71) Applicant: Ryan Anderson, San Diego, CA (US)

(72) Inventor: Ryan Anderson, San Diego, CA (US)

( * ) Notice: Subject to any disclaimer, the term of this patent is extended or adjusted under 35 U.S.C. 154(b) by 470 days.

(21) Appl. No.: 14/570,218

(22) Filed: Dec. 15, 2014

(65) Prior Publication Data
US 2015/0322389 A1    Nov. 12, 2015

Related U.S. Application Data

(60) Provisional application No. 61/996,439, filed on May 6, 2014.

(51) Int. Cl.
| | |
|---|---|
| *A47J 31/20* | (2006.01) |
| *A47B 13/06* | (2006.01) |
| *C12C 11/00* | (2006.01) |
| *C12C 13/10* | (2006.01) |
| *A47B 47/04* | (2006.01) |
| *B21D 47/04* | (2006.01) |
| *A47J 31/06* | (2006.01) |
| *A61B 50/10* | (2016.01) |
| *A61B 50/15* | (2016.01) |
| *A47B 7/00* | (2006.01) |
| *E04B 1/24* | (2006.01) |
| *E04C 3/04* | (2006.01) |
| *B01L 9/02* | (2006.01) |

(Continued)

(52) U.S. Cl.
CPC ............ *A47B 13/06* (2013.01); *A47B 47/047* (2013.01); *A47J 31/0636* (2013.01); *A47J 31/20* (2013.01); *A61B 50/10* (2016.02); *A61B 50/15* (2016.02); *B21D 47/04* (2013.01); *C12C 11/006* (2013.01); *C12C 13/10* (2013.01); *A47B 7/00* (2013.01); *A47B 2037/005* (2013.01); *A61B 2017/00526* (2013.01); *B01L 9/02* (2013.01); *E04B 2001/2415* (2013.01); *E04B 2001/2472* (2013.01); *E04C 2003/0413* (2013.01); *Y10T 403/479* (2015.01)

(58) Field of Classification Search
CPC ..... A47J 31/0636; A47J 31/0626; A47J 31/20
USPC .................... 99/322, 321, 317, 319
See application file for complete search history.

(56) References Cited

U.S. PATENT DOCUMENTS

| | | | |
|---|---|---|---|
| 530,149 A * | 12/1894 | Wilson .................. | A47J 31/02 99/322 |
| 1,018,684 A * | 2/1912 | Smith ................... | A47J 31/20 99/289 R |

(Continued)

*Primary Examiner* — Reginald L Alexander
(74) *Attorney, Agent, or Firm* — Coastal Patent Law Group, P.C.

(57) ABSTRACT

The disclosure concerns a filter assembly adapted for use with a wide mouth carboy in the field of home brewing, and home brewing kits comprising the same. The filter assembly generally includes a carboy lid adapted to engage a fermentation carboy, a mesh filter tube extending from a bottom side of the carboy lid, wherein through an aperture of the lid and into the volume within the mesh filter tube is defined a mesh cavity. Materials can be introduced into the mesh cavity for brewing applications. An agitation probe forms part of the home brewing kit and is used for: (i) agitating the materials within the mesh cavity during a brewing process; (ii) pressing the materials to extract fluids therefrom; or (iii) a combination thereof.

15 Claims, 5 Drawing Sheets

(51) Int. Cl.
*A47B 37/00* (2006.01)
*A61B 17/00* (2006.01)

(56) References Cited

U.S. PATENT DOCUMENTS

| | | | | |
|---|---|---|---|---|
| 2,055,096 A | * | 9/1936 | Dehn | A47J 31/0636 |
| | | | | 210/466 |
| 2,893,331 A | * | 7/1959 | Medlock | A47J 31/005 |
| | | | | 366/267 |
| 2008/0282900 A1 | * | 11/2008 | Huang | A47J 31/005 |
| | | | | 99/322 |
| 2015/0230651 A1 | * | 8/2015 | Molayem | A47J 31/0636 |
| | | | | 99/322 |

* cited by examiner

FILTER ASSEMBLY FOR USE WITH A WIDE-MOUTH FERMENTATION CARBOY

CROSS-REFERENCE TO RELATED APPLICATIONS

This application claims benefit of priority with U.S. Provisional Ser. No. 61/996,439, filed May 6, 2014, titled "Wide mouth carboy lid with filter mount and access port for dry hopping home brewed beer"; the contents of which are hereby incorporated by reference.

BACKGROUND

Field of the Invention

This invention relates to products for home brewing; and more particularly, to a filter assembly for use with a wide mouth carboy; and home brewing kits comprising the same.

Description of the Related Art

Home brewing of coffee and tea has long been practiced, and various products have been provided for home brewing. For example, tea or coffee grounds are conventionally placed in an apparatus and brewed with hot water to create a brewed drink.

In an effort to summarize the crowded art of home-brewing and beverage infusers, the following exemplary references are described.

U.S. Pat. No. 5,635,233, issued Jun. 3, 1997 to Melvin L. Levinson, titled "METHODS FOR PREPARING A COFFEE, TEA AND MILK BEVERAGE", describes a "French press" type brewing apparatus and related methods for preparing a beverage. The apparatus generally includes a vessel configured to receive water and solid material for brewing in the water; a plunger-strainer, and a lid. The plunger-strainer is used to strain the solid material from the brewed beverage. One problem with French press style brewing is that a volume of liquid remains in the bottom portion of the vessel subsequent to plunging/straining. This volume becomes waste. Moreover, the French press is not suitable for home brewing of beer and other alcohol-containing fermentation type beverages.

U.S. Pat. No. 5,996,473, issued Dec. 7, 1999 to Henry S. Milone, titled "BEVERAGE INFUSION DEVICE", describes a device configured to enable infusion of a beverage. The device includes a handle portion and a bore therethrough. Material is placed within the bore and a porous pouch is used to infuse the material with surrounding water when submerged therein for making a beverage. One problem with this device includes the submersion of the device, which makes for difficulty in removing from the liquid. Additionally, the material is not capable of being pressed to expel oils into the beverage liquid.

U.S. Pat. No. 6,684,756, issued Feb. 3, 2004 to Helen Kerr, titled "TEA INFUSER WITH MANUAL AGITATOR", describes an infuser vessel for containing solid particles while immersed in a liquid, such as loose tea leaves in hot water, where the perforated infuser vessel includes a manually moveable piston operated with a flexible wire topped with a manual grip extending upwardly from the liquid, whereby tea leaves within the vessel may be manually agitated to increase the speed and efficiency of infusion, while the manual grip remains high and dry above the liquid. Though this infuser is capable of agitating material when brewing, it is not capable of plunging to extract substantially the liquids and oils therein for communicating into the surrounding beverage.

In sum, conventional home brewing apparatuses are designed to infuse oils or flavors into liquids using a floating filter chamber and other techniques, but there has yet to be provided an infusing device capable of each of: (i) maintaining separation of solids from liquid in a brewing apparatus; (ii) agitating material within the device to enhance brewing efficiency; (iii) communicating substantially all oils and flavors from the device to the surrounding liquid; and (iv) removing the device from the surrounding liquid without penetrating a surface of the liquid to retrieve the device.

There is a modern trend in home brewing of alcohol-containing beverages, particularly wine and beer. In the home brewing of beer, it is sometimes advantageous to provide hops in a removeable filter such that the hops can be removed after boil. Moreover, certain beers benefit from the introduction of hops after fermentation known as "dry hopping", which provides added hop aroma and flavor to the finished beer.

There is a need for an improved hop filtering device for use in home brewing.

SUMMARY

A filter assembly adapted for use with a wide mouth carboy in the field of home brewing, and home brewing fermentation kits comprising the same, are each described in the embodiments herein.

The filter assembly generally includes a carboy lid adapted to engage a fermentation carboy, a mesh filter tube extending from a bottom side of the carboy lid, wherein through an aperture of the lid and into the volume within the mesh filter tube is defined a mesh cavity. Materials can be introduced into the mesh cavity for brewing applications. An agitation probe forms part of the home brewing kit and is used for: (i) agitating the materials within the mesh cavity during a brewing process; (ii) pressing the materials to extract fluids therefrom; or (iii) a combination thereof.

In certain embodiments, a home brewing fermentation kit comprises the filter assembly, an agitation probe, and a wide mouth fermentation carboy.

In the accompanying detailed description various preferred embodiments are described to enable those having skill in the art to make and use the same.

DETAILED DESCRIPTION

In the following description, for purposes of explanation and not limitation, details and descriptions are set forth in order to provide a thorough understanding of the embodiments of the invention. However, it will be apparent to those skilled in the art that the present invention may be practiced in other embodiments, including certain variations or alternative combinations that depart from these details and descriptions.

In one embodiment, a filter assembly for filtering material used in home brewing includes a carboy lid configured to engage with at least a portion of a fermentation carboy for attachment therewith. The carboy lid comprises a tubular flange extending from an aperture of the carboy lid. An elongated mesh tube extends from a sealed end to an open end with a volume therein forming a mesh cavity. The elongated mesh tube is configured to be liquid-permeable, and further configured to filter solids through a surface thereof. The elongated mesh tube is generally adapted to couple with the tubular flange of the carboy lid and extend into a volume of the fermentation carboy. The filter assembly is configured to receive an agitation probe inserted within the mesh cavity for agitating a mixture of the solids and liquid through the mesh tube.

In another embodiment, a filter assembly is configured for attachment with a wide-mouth fermentation carboy, the filter assembly comprises: a carboy lid, an elongated mesh tube coupled to the carboy lid and extending downwardly therefrom, and a cap configured for removeable engagement with the carboy lid for sealing a volume between the carboy lid and the attached wide-mouth fermentation carboy.

The carboy lid comprises: a bottom side, a top side opposite of the bottom side, a lid-aperture having a first diameter thereof, and a periphery. The carboy lid can further comprise: (i) at least a portion of material extending downwardly from the periphery to form a peripheral rim, the peripheral rim comprising an outer surface and an inner surface, wherein the inner surface of the peripheral rim further comprises threads configured to engage with at least a portion of the wide-mouth fermentation carboy for attachment therewith; (ii) a first tubular flange extending upwardly from the top side of the carboy lid at the lid-aperture; and (iii) a second tubular flange extending downwardly from the bottom side of the carboy lid at the lid-aperture.

The elongated mesh tube comprises a cylindrical mesh wall extending from a first open end to a second closed end forming a mesh cavity in a volume created therein. The open end of the elongated mesh tube is configured to couple with the carboy lid at the second tubular flange. The cylindrical mesh wall of the elongated mesh tube is generally liquid-permeable, and the mesh tube is configured with a mesh size for substantially retaining solids contained within the mesh cavity.

The cap is configured for removeable engagement with the upper flange of the carboy lid for sealing a volume between the carboy lid and the attached wide-mouth fermentation carboy.

Although certain features are shown having screw-type threads for engagement or attachment of various components it should be understood that generally any known mechanical attachment means may be utilized, including: threads, friction fits, clamps, adhesives, magnets, and the like.

Additionally, it is preferred to manufacture the carboy lid and cap from a polymer material or plastic; however, billet and cast metals may alternatively be used, for example, aluminum, steel, and the like. Other materials known by those having skill in the art may be sufficient for fabricating the carboy lid and/or the cap.

The agitation probe can be manufactured from plastic, however it is suggested that stainless steel or a similar material may provide the benefit of stain-resistance and also may be resistant to deformation due to applied heat.

Similarly, the mesh tube can be fabricated from a metal, plastic, or similar materials. Generally the mesh tube should have a mesh size sufficient to retain solids but also to communicate oils and liquids through the mesh wall.

The fermentation carboy is generally any glass or plastic carboy having a wide mouth diameter of three inches or greater. Such fermentation carboys are known in the art and available commercially.

Figure 1:
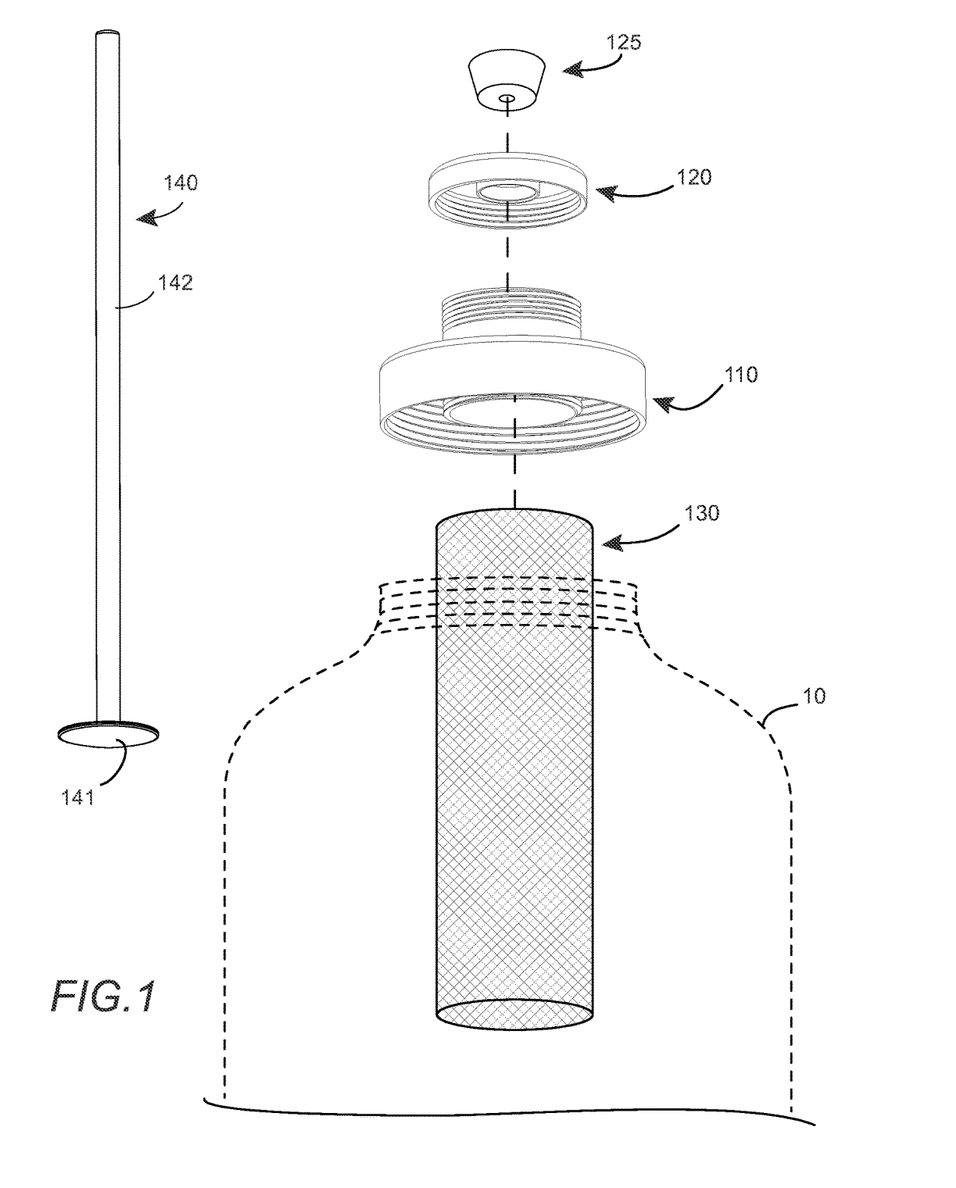
FIG. 1 shows an exploded view of a home brewing fermentation kit including a fermentation carboy, an agitation probe, and a filter assembly having each of: a carboy lid configured to engage an elongated mesh tube at an underside thereof, a cap configured to engage the carboy lid at an upper side thereof, and a stopper configured to seal an aperture about the cap.

Now turning to the drawings, FIG. 1 shows an exploded view of a home brewing fermentation kit including a fermentation carboy 10, an agitation probe 140, and a filter assembly having each of: a carboy lid 110 configured to engage an elongated mesh tube 130 at an underside thereof, a cap 120 configured to engage the carboy lid at an upper side thereof, and a stopper 125 configured to seal an aperture about the cap. The stopper comprises a drilled-stopper for inserting a fermentation lock (otherwise known as an "airlock") therethrough.

The fermentation carboy 10 is illustrated in dashed lines for indicating that such are commercially available and form part of the prior art.

The agitation probe 140 comprises a base 141 and a shaft 142 extending upwardly from the base. The base generally forms a disc having a probe diameter "$D_p$"; however other geometries can be implemented. The agitation probe is configured to insert through the carboy lid 110 with the cap 120 being removed, such that the agitation probe may be used to agitate material within the mesh cavity of the elongated mesh tube 130, and further be used to press the material for extracting substantially all of the oils and liquids from the filtered material in the mesh cavity. Note that the elongated mesh tube extends into a volume of the fermentation carboy, and that the extracted oils and liquids are easily communicated into the carboy volume.

The combination of the fermentation carboy 10, carboy lid 110, cap 120, stopper 125, and agitation probe 140 forms a home brewing fermentation kit with the novel filter assembly. Other accessories, such as a thermometer, fermentation lock, or other instruments may be optionally provided to form the home brewing fermentation kit.

Figure 2:
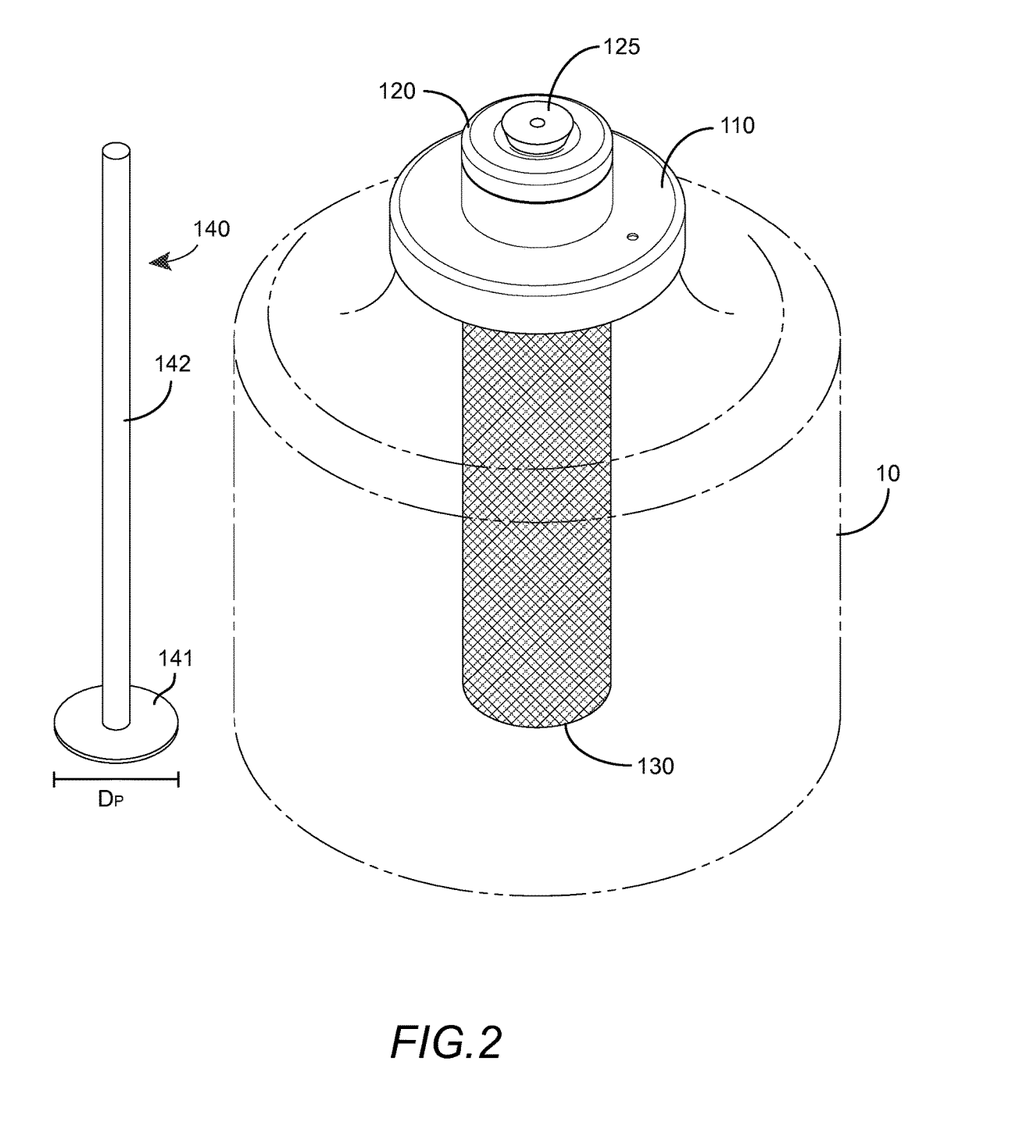
FIG. 2 shows the home brewing kit assembled and attached to the fermentation carboy.

FIG. 2 shows the home brewing kit assembled and attached to the fermentation carboy 10. The agitation probe 140 is stored outside of the carboy, and when needed is inserted through an aperture of the carboy lid 110 with the cap 120 and stopper 125 removed from the filter assembly. The base 141 of the agitation probe 140 has a diameter $D_p$ which is configured to fit through the aperture of the carboy lid into the mesh cavity of the elongated mesh tube 130. The elongated mesh tube 130 extends into an interior volume of the fermentation carboy 10.

Figure 3:
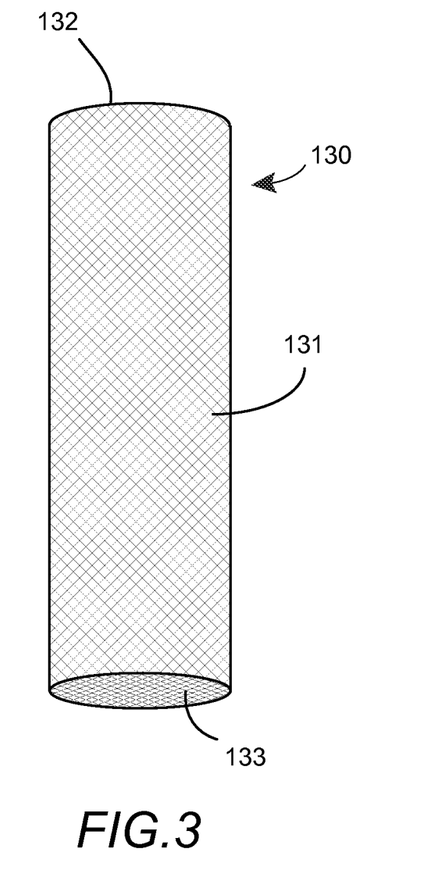
FIG. 3 shows a bottom perspective of the elongated mesh tube.

FIG. 3 shows a bottom perspective of the elongated mesh tube 130. The mesh tube comprises a cylindrical mesh wall 131 which extends downwardly from a first open end 132 to a second closed end 133.

Figure 4:
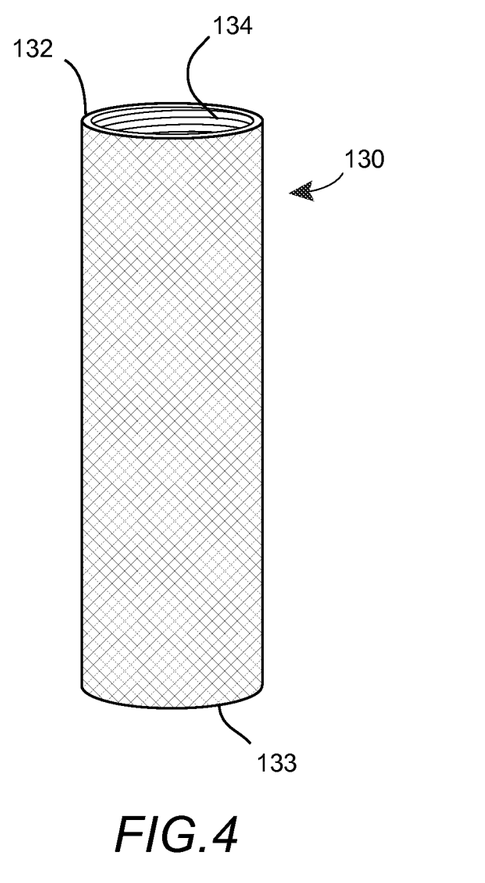
FIG. 4 shows a top perspective of the elongated mesh tube.

FIG. 4 shows a top perspective of the elongated mesh tube 130. In the illustrated embodiment, the mesh tube comprises mesh tube threads 134 disposed about an inner surface of the mesh tube at the first open end 132 thereof. The mesh tube threads serve to mate the elongated mesh tube to the carboy lid for attachment; however, other attachment means can be similarly implemented without departing from the scope of the invention.

Figure 5:
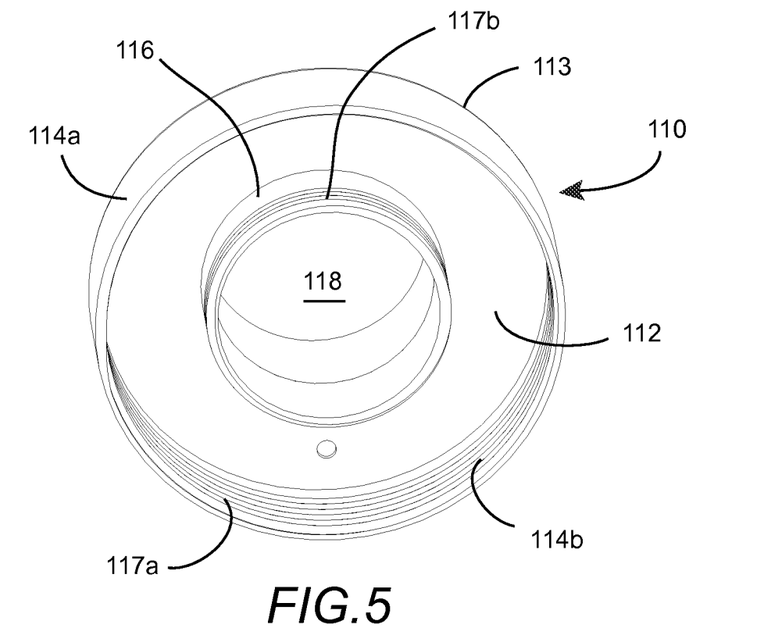
FIG. 5 shows a bottom perspective of the carboy lid.

FIG. 5 shows a bottom perspective of the carboy lid 110. The carboy lid 110 comprises a planar bottom side 112 opposite of a top side (111, FIG. 6) which extends radially outward from a lid aperture 118 to a periphery 113. A peripheral rim extends downwardly from the periphery and comprises an outer surface 114a and an inner surface 114b thereof, the peripheral rim is shown comprising threads 117a disposed about the inner surface of the peripheral rim configured to engage the fermentation carboy. A second tubular flange 116 extends downwardly about the lid aperture 118 from bottom side; the second tubular flange is shown comprising threads 117b for engaging the threads of the mesh tube. Although threads are illustrated, similar means can be implemented for attaching the mesh tube to the carboy lid, and the carboy lid to the fermentation carboy as desired by those with skill in the art, respectively.

Figure 6:
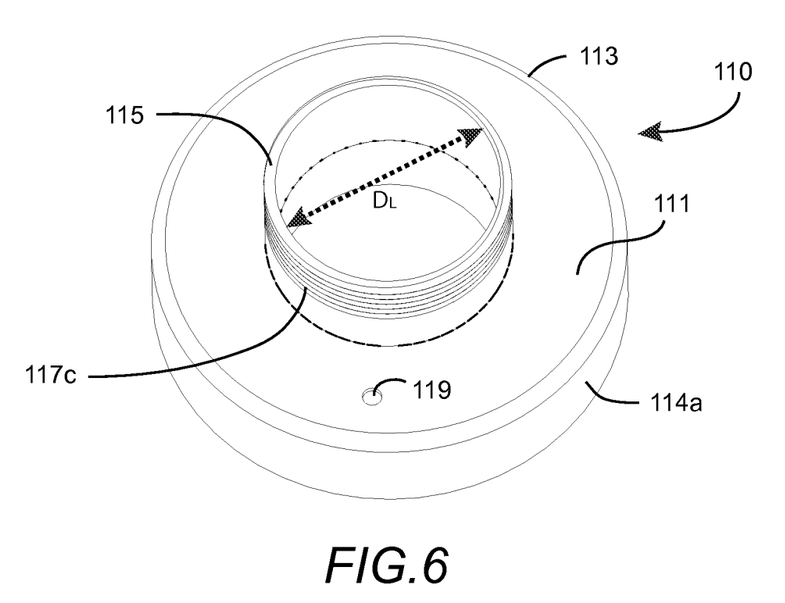
FIG. 6 shows a top perspective of the carboy lid.

FIG. 6 shows a top perspective of the carboy lid 110. The carboy lid comprises a planar top side 111 opposite of the bottom side (112, FIG. 5) which extends radially outward from the lid aperture 118 to the periphery 113. The peripheral rim is shown with outer surface 114a extending downwardly from the periphery. A first tubular flange 115 is shown extending upwardly from the aperture. Threads 117c are disposed about the first tubular flange 115 at a top end thereof. The first tubular flange and second tubular flange can comprise a monolithic cylinder extending through the carboy lid as shown, with the cylinder having a lid diameter "$D_L$" configured larger than the probe diameter of the agitation probe. A second lid aperture 119 can be provided. The second lid aperture 119 is generally configured to receive a thermometer (not shown).

In an alternative embodiment, the first and second tubular flanges can comprise two distinct flanges. In this embodiment it is advantageous to provide the first tubular flange with a lid diameter greater than the agitation probe, and the second tubular flange with a diameter thereof greater than the lid diameter of the first tubular flange. In this regard, the mesh tube can be significantly larger in diameter than the agitation probe.

Figure 7:
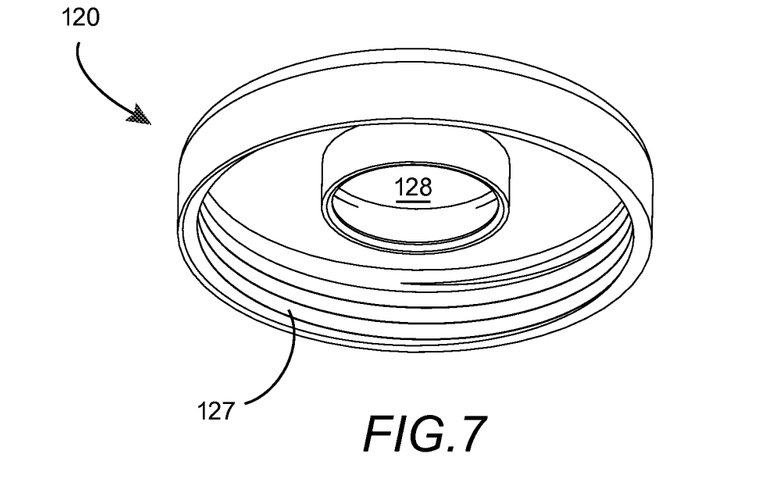
FIG. 7 shows a bottom perspective of the cap.

FIG. 7 shows a bottom perspective of the cap 120. The cap is shown comprising cap threads 127 disposed about a rim portion thereof, and a cap aperture 128 having a cap aperture flange extending downwardly therefrom.

Figure 8:
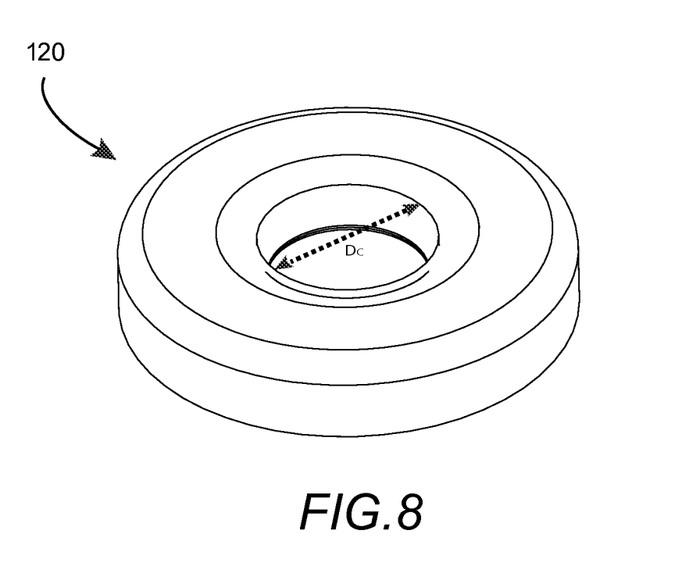
FIG. 8 shows a top perspective of the cap.

FIG. 8 shows a top perspective of the cap 120. The cap aperture comprises a diameter "$D_C$"; wherein DC is configured to receive and frictionally seal with a rubber, cork, or composite stopper (125, FIG. 1).

In an optional embodiment, the carboy lid can comprise a threaded ring and a disc configured to nest within the threaded ring, the threaded ring and disc forming a two-part lid, the disc configured to engage a filter and a cap as described above to yield a filter assembly similar in structure and utility.

Thus, the filter assembly generally comprises a carboy lid adapted to receive and removeably engage with an elongated mesh tube.

In another embodiment, a cap is not required and a stopper is used to seal a flange of the carboy lid. When the stopper is removed the agitation probe can be inserted.

In various embodiments, the carboy lid can be modified to further comprise an O-ring or other seal for sealing a mated surface between the carboy lid and the fermentation carboy. In one embodiment the O-ring or seal is configured to abut a top surface of the carboy and the bottom side of the carboy lid. In another embodiment, an O-ring is embedded in a channel extending about the inner surface of the peripheral rim, the O-ring being configured to seal a mated surface of the carboy and the carboy lid.

In various embodiments, the lid aperture is disposed in a center of the carboy lid.

In various other embodiments, the lid aperture is disposed adjacent to a center of the carboy lid, or off to a side thereof. In this embodiment an optional second aperture can be provided for use with a thermometer or a stopper. Moreover, a threaded cap, such as a PVC cap can assume the function of the rubber-stopped cap in some of these various embodiments.

The agitation probe can be used with the filter assembly installed and expanding into the fermentation carboy for agitating and communicating oils through the mesh wall; however, the filter assembly can also be conveniently removed substantially from the volume of the carboy such that the oils can be extracted, using the probe, with the filter assembly being removed from the carboy volume. In this regard, a significant amount of liquid can be extracted from the filter when removed from the carboy volume for minimizing waste and maximizing flavoring of a brewed batch.

| REFERENCE CHARACTERS |
| --- |
| Fermentation carboy 10 |
| Carboy lid 110 |
| Carboy lid top side 111 |
| Carboy lid bottom side 112 |
| Carboy lid periphery 113 |
| Peripheral rim outer surface 114a |
| Peripheral rim inner surface 114b |
| First tubular flange 115 |
| Second tubular flange 116 |
| Threads 117a; 117b; 117c |
| Lid aperture 118 |
| Second lid aperture 119 |
| Lid aperture diameter $D_L$ |
| Cap 120 |
| Stopper 125 |
| Cap threads 127 |
| Cap aperture 128 |
| Cap aperture diameter $D_C$ |
| Elongated mesh filter 130 |
| Cylindrical mesh wall 131 |
| Mesh tube top end 132 |
| Mesh tube bottom end 133 |
| Mesh tube threads 134 |
| Agitation probe 140 |
| Probe base 141 |
| Probe shaft 142 |
| Probe diameter $D_P$ |

What is claimed is:

1. A filter assembly configured for attachment with a wide-mouth fermentation carboy, the filter assembly comprising:
a carboy lid comprising a bottom side, a top side opposite of the bottom side, a lid-aperture having a first diameter thereof, and a periphery, the carboy lid further comprising:
at least a portion of material extending downwardly from the periphery to form a peripheral rim, said peripheral rim comprising an outer surface and an inner surface, wherein said inner surface of the peripheral rim further comprises threads configured to engage with at least a portion of said wide-mouth fermentation carboy for attachment therewith;
a first tubular flange extending upwardly from the top side of the carboy lid at the lid-aperture; and
a second tubular flange extending downwardly from the bottom side of the carboy lid at the lid-aperture;

the filter assembly further comprising:
an elongated mesh tube comprising a cylindrical mesh wall extending from a first open end to a second closed end and forming a mesh cavity therein, said open end of the elongated mesh tube being configured to couple with the carboy lid at the second tubular flange, the cylindrical mesh wall being liquid-permeable, and said mesh tube being configured with a mesh size for substantially retaining solids contained within the mesh cavity; and
a cap configured for removeable engagement with the upper flange of the carboy lid for sealing a volume between the carboy lid and the attached wide-mouth fermentation carboy;
the cap comprising a cap-aperture disposed at a center of the cap, said cap-aperture having a second diameter thereof; and
the cap being configured to receive a stopper for sealing an area about the cap-aperture.

2. The filter assembly of claim 1, wherein said lid-aperture is disposed at a center of the carboy lid.

3. The filter assembly of claim 1, said stopper comprising a drilled-stopper configured to receive a fermentation lock through a drilled hole thereof.

4. The filter assembly of claim 1, wherein said filter assembly is configured to receive an agitation probe inserted through the lid-aperture, said agitation probe comprising a base and a shaft extending upwardly therefrom, the base being configured in size for insertion through the lid-aperture.

5. The filter assembly of claim 4 configured to receive said agitation probe for agitating a mixture of the solids contained within the mesh cavity and an amount of liquid therein.

6. The filter assembly of claim 4, wherein said agitation probe is configured to compress the solids within the mesh cavity about the elongated mesh tube for communicating material from within the mesh cavity into a volume of the carboy outside of the mesh tube.

7. The filter assembly of claim 1, wherein said elongated mesh tube is coupled to said second tubular flange via an engagement of threads thereof.

8. The filter assembly of claim 1, wherein said cap is configured for removable engagement with the upper flange via an engagement of threads thereof.

9. The filter assembly of claim 1, said carboy lid comprising a two-part lid having a threaded ring and a planar disc configured to nest within the planar ring, the disc forming the top and bottom sides and the lid aperture being disposed on the disc.

10. A filter assembly configured for attachment with a wide-mouth fermentation carboy, the filter assembly comprising:
a carboy lid comprising a bottom side, a top side opposite of the bottom side, a first lid-aperture having a first diameter thereof, and a periphery, the carboy lid further comprising:
at least a portion of material extending downwardly from the periphery to form a peripheral rim, said peripheral rim comprising an outer surface and an inner surface, wherein said inner surface of the peripheral rim further comprises threads configured to engage with at least a portion of said wide-mouth fermentation carboy for attachment therewith;
a first tubular flange extending upwardly from the top side of the carboy lid at the first lid-aperture;
a second tubular flange extending downwardly from the bottom side of the carboy lid at the first lid-aperture; and
a second lid aperture, wherein said second lid aperture is configured to receive a thermometer therethrough;
the filter assembly further comprising:
an elongated mesh tube comprising a cylindrical mesh wall extending from a first open end to a second closed end and forming a mesh cavity therein, said open end of the elongated mesh tube being configured to couple with the carboy lid at the second tubular flange, the cylindrical mesh wall being liquid-permeable, and said mesh tube being configured with a mesh size for substantially retaining solids contained within the mesh cavity; and
a cap configured for removeable engagement with the upper flange of the carboy lid for sealing a volume between the carboy lid and the attached wide-mouth fermentation carboy.

11. A filter assembly configured for attachment with a fermentation carboy, the filter assembly comprising:
a carboy lid configured to engage with at least a portion of said fermentation carboy for attachment therewith, the carboy lid further comprising a tubular flange extending from an aperture of the carboy lid;
a cap configured for removeable engagement with the carboy lid for sealing a volume between the carboy lid and the fermentation carboy, the cap comprising
a cap-aperture disposed at a center of the cap, said cap-aperture having a diameter thereof being configured to receive: a stopper for sealing an area about the cap-aperture, a fermentation lock, or a combination thereof; and
the filter assembly further comprising:
an elongated mesh tube extending from a sealed end to an open end with a volume therein forming a mesh cavity, the elongated mesh tube being liquid-permeable and configured to filter solids through a surface thereof, the elongated mesh tube further configured to couple with the tubular flange of the carboy lid and extend into a volume of the fermentation carboy;
wherein said filter assembly is configured to receive an agitation probe inserted within the mesh cavity for agitating a mixture of the solids and liquid through the mesh tube.

12. A fermentation infusion kit, the kit comprising:
a fermentation carboy;
a carboy lid configured to engage with at least a portion of said fermentation carboy for attachment therewith, the carboy lid further comprising a tubular flange extending from an aperture of the carboy lid;
a cap configured for removeable engagement with the carboy lid, the cap including a cap-aperture disposed at a center of the cap, the cap-aperture having a diameter thereof being configured to receive: a stopper for sealing an area about the cap-aperture, a fermentation lock, or a combination thereof; and
an elongated mesh tube extending from a sealed end to an open end with a volume therein forming a mesh cavity, the elongated mesh tube being liquid-permeable and configured to filter solids through a surface thereof, the elongated mesh tube further configured to couple with the tubular flange of the carboy lid and extend into a volume of the fermentation carboy with the lid attached therewith; and
an agitation probe configured for insertion within the mesh cavity.

13. The fermentation kit of claim 12, wherein said agitation probe is configured to: agitate the solids and liquids within the mesh cavity; compress the solids within the mesh cavity for communicating oils and liquid into the fermentation carboy; or a combination thereof.

14. The fermentation kit of claim 12, said agitation probe comprising a base and a shaft extending upwardly therefrom, the base being configured in size for insertion through the lid-aperture.

15. The fermentation kit of claim 12, wherein said base of the probe comprises a probe diameter that is smaller than a diameter of the tubular flange for inserting said probe through said carboy lid aperture into the mesh cavity of the elongated mesh tube.

\* \* \* \* \*